United States Patent
Namiki

(10) Patent No.: US 11,963,825 B2
(45) Date of Patent: Apr. 23, 2024

(54) APPARATUS AND DATA PROCESSING METHOD

(71) Applicant: CANON MEDICAL SYSTEMS CORPORATION, Otawara (JP)

(72) Inventor: Kousuke Namiki, Otawara (JP)

(73) Assignee: CANON MEDICAL SYSTEMS CORPORATION, Otawara (JP)

(*) Notice: Subject to any disclaimer, the term of this patent is extended or adjusted under 35 U.S.C. 154(b) by 385 days.

(21) Appl. No.: 17/219,944

(22) Filed: Apr. 1, 2021

(65) Prior Publication Data

US 2021/0307725 A1 Oct. 7, 2021

(30) Foreign Application Priority Data

Apr. 6, 2020 (JP) .................................. 2020-068541

(51) Int. Cl.
*A61B 8/00* (2006.01)
*A61B 8/06* (2006.01)
(Continued)

(52) U.S. Cl.
CPC ............ *A61B 8/5223* (2013.01); *A61B 8/065* (2013.01); *A61B 8/488* (2013.01); *A61B 8/5269* (2013.01);
(Continued)

(58) Field of Classification Search
CPC ....... A61B 8/5223; A61B 8/065; A61B 8/488; A61B 8/5269; A61B 8/5284; G06T 7/70;
(Continued)

(56) References Cited

U.S. PATENT DOCUMENTS

2005/0015009 A1* 1/2005 Mourad ............... A61B 5/0051
600/453
2006/0052704 A1* 3/2006 Baba ................... G01S 15/8981
600/453
(Continued)

FOREIGN PATENT DOCUMENTS

JP 2002-291749 A 10/2002
JP 2006-102489 A 4/2006
(Continued)

OTHER PUBLICATIONS

Bishop, "Pattern Recognition and Machine Learning", vol. 1, Springer, 2006, (pp. 225-290) 758 pages.
(Continued)

*Primary Examiner* — Michael R Neff
(74) *Attorney, Agent, or Firm* — Oblon, McClelland, Maier & Neustadt, L.L.P.

(57) ABSTRACT

An apparatus according to an embodiment includes a processing circuit. The processing circuit is configured to obtain first Doppler waveform data related to a left ventricular blood inflow. The processing circuit is configured to detect positions of an E-wave and an A-wave in the first Doppler waveform data, by using the first Doppler waveform data and a trained model trained with training data that includes at least positions of an E-wave and an A-wave in each of a plurality of pieces of second Doppler waveform data related to left ventricular blood inflows and the plurality of pieces of second Doppler waveform data.

16 Claims, 8 Drawing Sheets

(51) Int. Cl.
- *A61B 8/08* (2006.01)
- *G06T 7/70* (2017.01)
- *G16H 50/20* (2018.01)

(52) U.S. Cl.
CPC .............. *A61B 8/5284* (2013.01); *G06T 7/70* (2017.01); *G16H 50/20* (2018.01); *G06T 2207/10132* (2013.01); *G06T 2207/20081* (2013.01); *G06T 2207/30048* (2013.01)

(58) Field of Classification Search
CPC . G06T 2207/10132; G06T 2207/20081; G06T 2207/30048; G16H 50/20
USPC ........................................................ 382/128
See application file for complete search history.

(56) References Cited

U.S. PATENT DOCUMENTS

| | | | |
|---|---|---|---|
| 2009/0310837 A1* | 12/2009 | Park ..................... | A61B 8/488 382/128 |
| 2020/0060656 A1 | 2/2020 | Chono | |
| 2020/0085410 A1* | 3/2020 | Banjanin .............. | A61B 8/0883 |

FOREIGN PATENT DOCUMENTS

| | | |
|---|---|---|
| JP | 2006-141997 A | 6/2006 |
| JP | 2010-200844 A | 9/2010 |
| JP | 2015-116331 A | 6/2015 |
| WO | WO 2018/207474 A1 | 11/2018 |

OTHER PUBLICATIONS

Japanese Office Action dated Oct. 17, 2023, in Japanese Application No. 2020-068541, citing documents 15,24-25 therein, 2 pgs,.

Eleonora Sulas, et al., Automatic Recognition of Complete Atrio-ventricular Activity in Fetal Pulsed-Wave Doppler Signals, Annual International Conference of the IEEE Engineering in Medicine and Biology Society (EMBC), 2018, pp. 917-920.

Noriko Tomita, et al., "Evaluation of the ability to dilate left ventricular by echocardiography", Heart, 2013, vol. 45, No. 7, pp. 753-760 with partial English translation.

Japanese Office Action dated Feb. 20, 2024, in Japanese Patent Application No. 2020-068541, citing documents 15-16, therein, 2 pages.

* cited by examiner

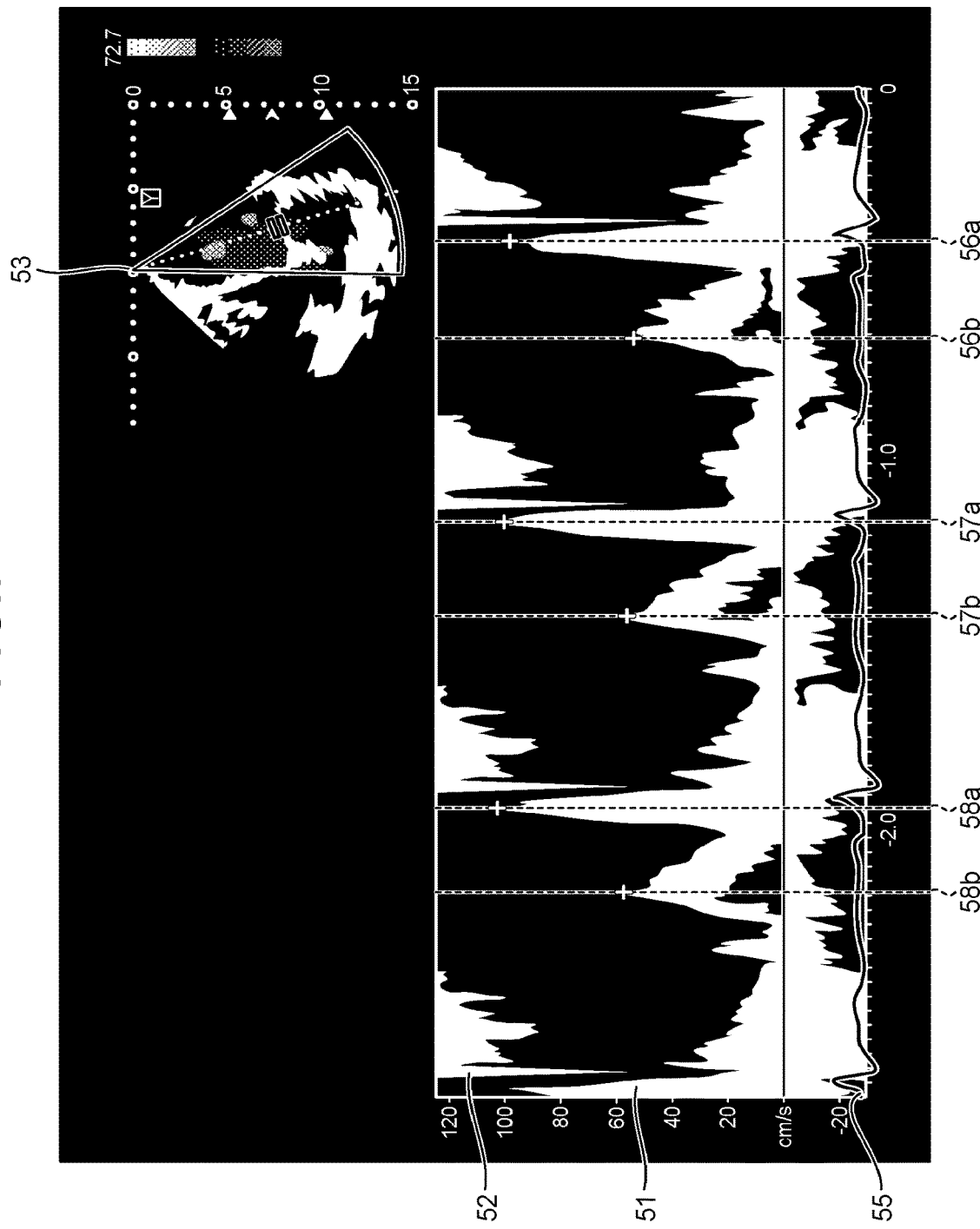

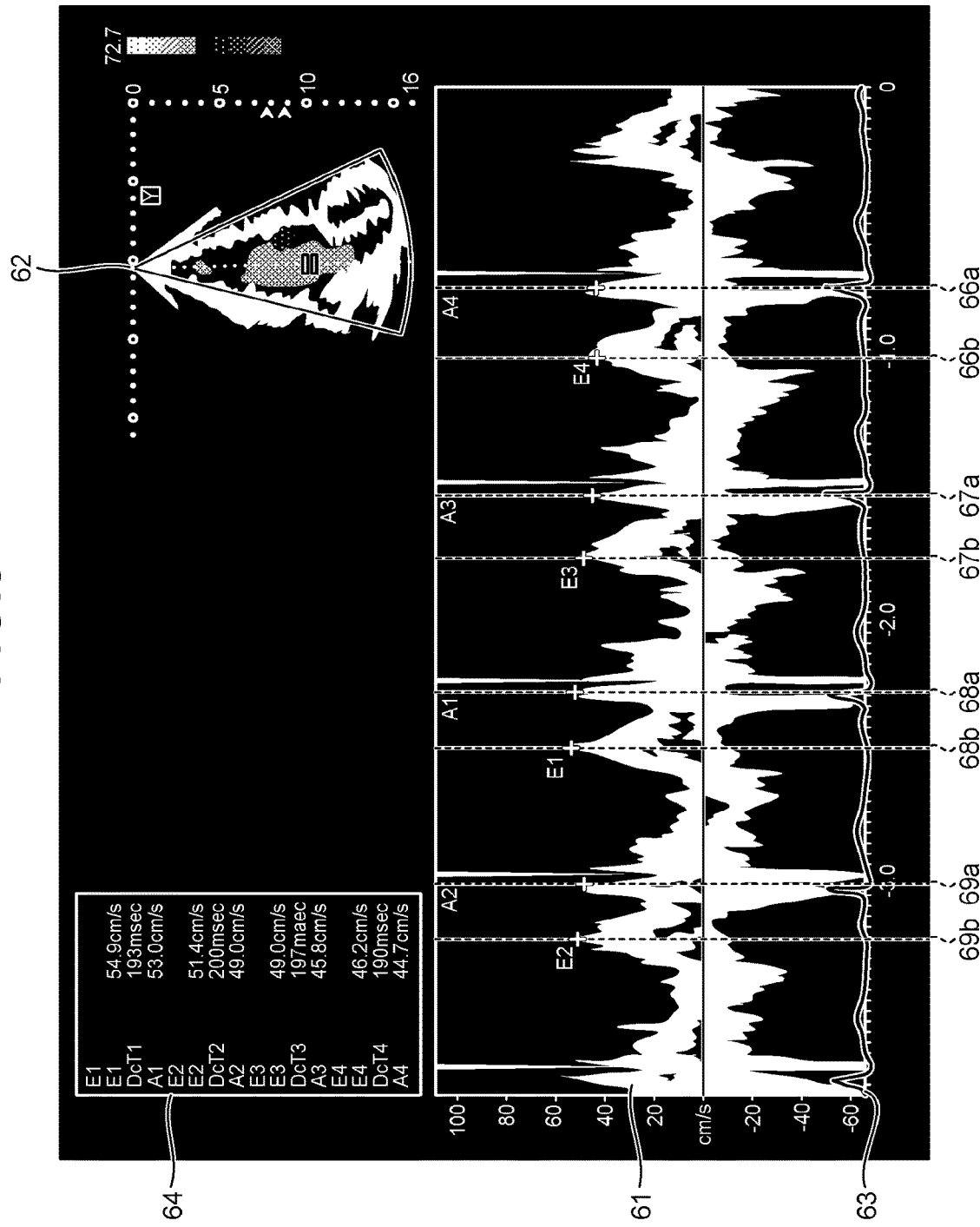

APPARATUS AND DATA PROCESSING METHOD

CROSS-REFERENCE TO RELATED APPLICATIONS

This application is based upon and claims the benefit of priority from Japanese Patent Application No. 2020-068541, filed on Apr. 6, 2020; the entire contents of which are incorporated herein by reference.

FIELD

Embodiments described herein relate generally to an apparatus and a data processing method.

BACKGROUND

For example, to diagnose a mitral valve regurgitation, the left ventricular blood inflow is imaged by using a pulse Doppler scheme. From an obtained image rendering a Doppler waveform (a Doppler waveform image), an Early Wave (an E-Wave), an Atrium Wave (an A-wave), and Deceleration Time (DcT) of the E-wave are identified. The E-wave and the like in the Doppler waveform image are identified by using an algorithm calculation or by humans.

When the Doppler waveform image contains much noise, aliasing, or the like, however, there is a possibility that conventional methods may fail to accurately identify the positions of the E-wave and the A-wave.

BRIEF DESCRIPTION OF THE DRAWINGS

FIG. 7 is a drawing illustrating an example of a Doppler mode display screen that includes aliasing waveform data and is used for generating the trained model; and FIG. 8 is a drawing illustrating an example of a Doppler mode display screen that includes normal waveform data and is used for generating the trained model.

DETAILED DESCRIPTION

Figure 1:
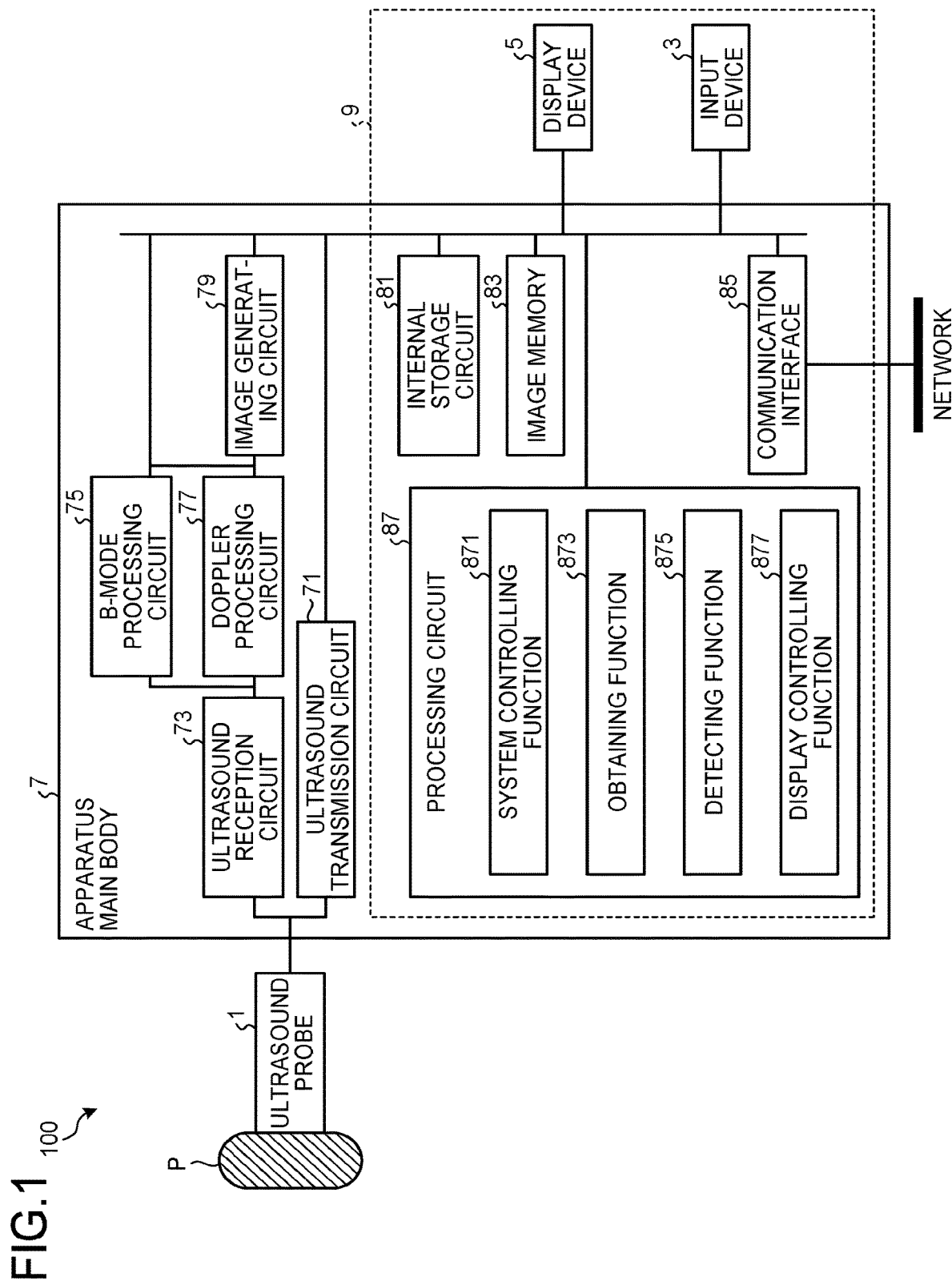
FIG. 1 is a diagram illustrating an exemplary configuration of an ultrasound diagnosis apparatus according to an embodiment.

An apparatus according to an embodiment includes a processing circuit. The processing circuit is configured to: obtain first Doppler waveform data related to a left ventricular blood inflow; and to detect positions of an E-wave and an A-wave in the first Doppler waveform data, by using the first Doppler waveform data and a trained model trained with training data that includes at least positions of an E-wave and an A-wave in each of a plurality of pieces of second Doppler waveform data related to left ventricular blood inflows and the plurality of pieces of second Doppler waveform data.

Exemplary embodiments of an apparatus and a program will be explained below, with reference to the accompanying drawings. To explain the embodiments specifically, an ultrasound diagnosis apparatus will be explained as an example of the apparatus according to an embodiment of the present disclosure. In the embodiments described below, some of the constituent elements having mutually the same reference characters are assumed to perform mutually the same operation, and duplicate explanations thereof will be omitted as appropriate.

Embodiments

FIG. 1 is a diagram illustrating an exemplary configuration of an ultrasound diagnosis apparatus 100 according to the present embodiment. As illustrated in FIG. 1, the ultrasound diagnosis apparatus 100 includes an ultrasound probe 1, an input device 3, a display device (a display unit) 5, and an apparatus main body 7.

The ultrasound probe 1 includes a plurality of piezoelectric transducer elements, a matching layer provided for the piezoelectric transducer elements, a backing member that prevents ultrasound waves from propagating rearward from the piezoelectric transducer elements, and the like. The ultrasound probe 1 is detachably connected to the apparatus main body 7. The plurality of piezoelectric transducer elements are configured to generate the ultrasound waves on the basis of a drive signal supplied thereto from an ultrasound transmission circuit 71 included in the apparatus main body 7. Further, the ultrasound probe 1 may be provided with a button pressed to perform various types of operations such as a freeze operation.

When an ultrasound wave is transmitted from the ultrasound probe 1 to an examined subject (hereinafter, "patient") P, the transmitted ultrasound wave is repeatedly reflected on a surface of discontinuity of acoustic impedances at a tissue in the body of the patient P. The reflected ultrasound wave is received as a reflected-wave signal (hereinafter, "echo signal") by the plurality of piezoelectric transducer elements included in the ultrasound probe 1. The amplitude of the received echo signal is dependent on the difference between the acoustic impedances on the surface of discontinuity on which the ultrasound wave is reflected. When a transmitted ultrasound pulse is reflected on the surface of a moving blood flow, a cardiac wall, or the like, the echo signal is, due to the Doppler effect, subject to a frequency shift, depending on a velocity component of the moving members with respect to the ultrasound wave transmission direction. The ultrasound probe 1 is configured to receive the echo signal from the patient P and to convert the echo signal into an electrical signal. In the present embodiment, the ultrasound probe 1 may be, for example, a one-dimensional (1D) array probe in which the plurality of piezoelectric transducer elements are arranged along a predetermined direction, a two-dimensional (2D) array probe in which the plurality of piezoelectric transducer elements are arranged in a two-dimensional matrix formation, a mechanical four-dimensional (4D) probe capable of performing an ultrasound scan while mechanically swaying an array of piezoelectric transducer elements in the directions orthogonal to the array direction, or the like.

The input device 3 is configured to receive various types of input operations from an operator, to convert the received input operations into electrical signals, and to output the electrical signals to a processing circuit 87. The input device 3 includes, for example, a mouse, a keyboard, a trackball, a switch, a button, a joystick, a touchpad, a touch panel display device, and/or the like. In the present embodiment, the input device 3 does not necessarily have to include one or more physical operational component parts such as the mouse, the keyboard, the trackball, the switch, the button, the joystick, the touchpad, the touch panel display device, and/or the like. Examples of the input device 3 include, for instance, an electrical signal processing circuit configured to receive electrical signals corresponding to input operations from an external input device provided separately from the input device 3 and to output the electrical signals to the processing circuit 87. Alternatively, the input device 3 may be included in the apparatus main body 7. In another example, the input device 3 may be configured by using a tablet terminal or the like capable of wirelessly communicating with the apparatus main body 7.

For example, in response to an end button on the input device 3 being pressed or the freeze button being pressed (hereinafter, "a freeze operation"), the ultrasound diagnosis apparatus 100 is configured to halt the transmission and reception of the ultrasound wave and to go into a paused state.

Further, in response to a freeze operation through the input device 3 during a B-mode scan, the ultrasound diagnosis apparatus 100 is configured to transition from a real-time display mode in which an ultrasound image generated from the transmission and reception of ultrasound waves is displayed in a real-time manner, into a cine display mode in which a plurality of ultrasound images stored in an image memory 83 are displayed in a time series (hereinafter, "cine display").

Further, in response to a freeze operation through the input device 3 during a Doppler mode scan, the ultrasound diagnosis apparatus 100 is configured to transition from a real-time display mode in which a Doppler waveform generated from the transmission and reception of ultrasound waves is displayed in a real-time manner, into a scroll display mode. In this situation, the scroll display mode denotes a mode in which it is possible to display a plurality of Doppler waveform images stored in the image memory 83 so as to be scrolled in the chronological order or in the reverse chronological order. For example, in the scroll display mode, when the operator rotates the trackball or the like, the ultrasound diagnosis apparatus 100 is configured to read and display Doppler waveform images corresponding to the rotation direction and the rotation amount of the trackball, from among the plurality of Doppler waveform images stored in the image memory 83. The rotation of the trackball corresponds to a scroll operation to scroll, in the chronological order or in the reverse chronological order, the Doppler waveform images in a time series, after a freeze operation is input.

The display device 5 is an arbitrary display device such as a Liquid Crystal Display (LCD) device, a Cathode Ray Tube (CRT) display device, an Organic ElectroLuminescence Display (OELD) device, or a plasma display device, for example. Alternatively, the display device 5 may be incorporated in the apparatus main body 7. Further, the display device 5 may be of a desktop type or may be configured by using a tablet terminal or the like capable of wirelessly communicating with the apparatus main body 7. The display device 5 is an example of a display unit.

The display device 5 is configured to display various types of information. For example, the display device 5 is configured to display ultrasound images generated by the processing circuit 87 or an image generating circuit 79, a user interface (hereinafter, "Graphical User Interface [GUI]") used for receiving various types of operations from the operator, and the like. In the cine display mode, the display device 5 is configured to display the ultrasound images in the time series, according to an instruction from the operator via the input device 3. In the scroll display mode, the display device 5 is configured to display the Doppler waveform images in the time series according to an instruction from the operator via the input device 3. As another example, in the Doppler mode, the display device 5 is configured, when the scroll operation is input after a freeze operation is input (the scroll display), to display a Doppler waveform corresponding to at least one corresponding heartbeat in accordance with the direction and the amount of the scroll operation.

The apparatus main body 7 is an apparatus configured to generate the ultrasound images on the basis of the echo signal received by the ultrasound probe 1. As illustrated in FIG. 1, the apparatus main body 7 includes the ultrasound transmission circuit 71, an ultrasound reception circuit 73, a B-mode processing circuit 75, a Doppler processing circuit 77, the image generating circuit 79, an internal storage circuit (a storage unit) 81, the image memory 83 (which may be referred to as a cine memory or a cache), a communication interface 85, and the processing circuit 87.

The ultrasound transmission circuit 71 is a processor configured to supply the drive signal to the ultrasound probe 1. The ultrasound transmission circuit 71 includes, for example, a trigger generating circuit, a delay circuit, and a pulser circuit, or the like. By employing a system controlling function 871 included in the processing circuit 87, the trigger generating circuit is configured to repeatedly generate, at a prescribed rate frequency, a rate pulse for forming a transmission ultrasound wave. The delay circuit is configured to apply a delay time period corresponding to each piezoelectric transducer element and required to determine transmission directionality by converging the ultrasound waves generated from the ultrasound probe 1 in a beam form, to each of the rate pulses. By employing the system controlling function 871, the pulser circuit is configured to apply the drive signal (a drive pulse) to the ultrasound probe 1 with timing based on the rate pulses. As a result of the delay circuit varying the delay time periods applied to the rate pulses, it is possible to arbitrarily adjust transmission direction from the surfaces of the piezoelectric transducer elements.

The ultrasound reception circuit 73 is a processor configured to generate a reception signal by performing any of various types of processes on the echo signal received by the ultrasound probe 1. The ultrasound reception circuit 73 includes, for example, an amplifier circuit, an Analog/Digital (A/D) converter, a reception delay circuit, and an adder, or the like. The amplifier circuit is configured to amplify the echo signal received by the ultrasound probe 1 for each channel and to perform a gain correcting process on the amplified echo signals. The A/D converter is configured to convert the gain-corrected echo signals into digital signals. The reception delay circuit is configured to apply delay time periods required to determine reception directionality, to the digital signals. The adder is configured to add together the plurality of digital signals to which the delay periods have been applied. As a result of the adding process by the adder, the reception signal is generated in which a reflection component from the direction corresponding to the reception directionality is emphasized.

The B-mode processing circuit 75 is a processor configured to generate B-mode data on the basis of the reception signal received from the ultrasound reception circuit 73. The B-mode processing circuit 75 is configured to generate data (i.e., data obtained in a B-mode; hereinafter, "B-mode data") in which the signal intensity is expressed by a degree of brightness, by performing an envelope detecting process and a logarithmic amplification process, or the like, on the reception signal received from the ultrasound reception circuit 73. The generated B-mode data is stored in a raw data memory (not illustrated) as B-mode raw data on two-dimensional ultrasound scanning lines.

The Doppler processing circuit 77 is a processor configured to generate Doppler waveform data and Doppler data on the basis of the reception signal received from the ultrasound reception circuit 73. The Doppler processing circuit 77 is configured to extract a blood flow signal from the reception signal, to generate the Doppler waveform data from the extracted blood flow signal, and to also generate data (i.e., data obtained in the Doppler mode; hereinafter, "Doppler data") obtained by extracting an average velocity value, dispersion, power, and the like with respect to multiple points from the blood flow signal. The generated Doppler data is stored in the raw data memory (not illustrated) as Doppler raw data on two-dimensional ultrasound scanning lines.

The image generating circuit 79 is configured to generate a GUI used by the operator to input various types of instructions via the input device 3. The image generating circuit 79 is a processor having a function (a scan converter) configured to generate data of various types of ultrasound images, on the basis of the data generated by the B-mode processing circuit 75 and the Doppler processing circuit 77. The image generating circuit 79 includes an internal memory (not illustrated). By performing a raw-pixel conversion, the image generating circuit 79 is configured to generate two-dimensional ultrasound image data (e.g., B-mode image data, color Doppler image data, Doppler waveform image data, etc.) structured with pixels. The image generating circuit 79 is configured to store the generated ultrasound image data into the internal storage circuit 81. The image generating circuit 79 is configured to perform various types of image processing processes such as correcting a dynamic range, brightness levels, contrast, and/or a γ curve as well as an RGB conversion or the like, on the generated ultrasound image data.

Further, the image generating circuit 79 is also capable of generating volume data structured with voxels in a desired range, by performing an interpolation process or the like that takes spatial position information into account, on the B-mode image data or the like. Further, the image generating circuit 79 may also generate volume data by performing a raw-voxel conversion including an interpolation process that takes spatial position information into account, on the B-mode raw data stored in the raw data memory. Furthermore, the image generating circuit 79 may generate a rendering image and a Multi Planar Reconstruction (MPR) image by performing, for example, a rendering process and a Multi Planar Reconstruction (MPR) process, or the like, on various types of volume data.

For example, the internal storage circuit 81 is realized by using a magnetic or optical storage medium, a storage medium readable by a processor such as an integrated circuit storage device, or the like. For example, the internal storage circuit 81 corresponds to a Hard Disk Drive (HDD), a Solid State Driver (SSD), a semiconductor memory, or the like that has various types of information stored therein. Other than an HDD or an SSD, the internal storage circuit 17 may be a drive device configured to read and write various types of information from and to a portable storage medium such as a Compact Disc (CD), a Digital Versatile Disc (DVD), or a flash memory, or a semiconductor memory such as a Random Access Memory (RAM).

The internal storage circuit 81 is configured to store therein programs for realizing various types of functions according to the present embodiment, and the like. The internal storage circuit 81 stores therein a group of data including diagnosis information (e.g., patient IDs, medical doctors' observations, etc.), diagnosis protocols, a body mark creating program, and a conversion table that sets, in advance, a range of color data used for visualization for each diagnosed site. The various types of data stored in the internal storage circuit 81 may also be transferred by the system controlling function 871 to an external device via a communication interface. The internal storage circuit 81 is configured to store a trained model therein. Alternatively, the trained model may be stored in a memory of the processing circuit 87 itself. The trained model is brought into operation by a detecting function 875 included in the processing circuit 87, to detect an E-wave and an A-wave (hereinafter, "E-wave/A-wave detecting process") of flow velocity related to the left ventricular blood inflow in the vicinity of the mitral valve.

Figure 2:
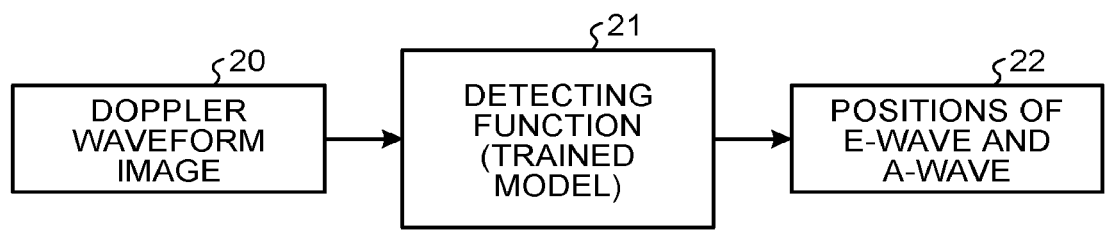
FIG. 2 is a diagram illustrating an example of a relationship between inputs and outputs of a trained model at the time of operation to detect an E-wave and an A-wave.

FIG. 2 is a diagram illustrating an example of a relationship between inputs and outputs of the trained model 21 at the time of the operation to perform the E-wave/A-wave detecting process. As illustrated in FIG. 2, upon receipt of an input of Doppler waveform image data 20, the trained model 21 is configured to output the E-wave and the A-wave in a Doppler waveform within the Doppler waveform image data 20, as a result of the E-wave/A-wave detecting process. In other words, the trained model 21 is a model trained with training data that includes at least the positions of an E-wave and an A-wave 22 in each of a plurality of pieces of Doppler waveform image data 20 (the plurality of pieces of second Doppler waveform data) related to the left ventricular blood inflow and the plurality of pieces of Doppler waveform image data 20. More specifically, as the E-wave/A-wave detecting process, the trained model 21 is configured to receive the input of the Doppler waveform image data 20 and to output the coordinates of the E-wave and the A-wave in the Doppler waveform within the Doppler waveform image data being input.

It is sufficient when the Doppler waveform image data 20 input to the trained model 21 includes a Doppler waveform corresponding to at least one heartbeat. When the Doppler waveform image data input to the trained model 21 includes a Doppler waveform corresponding to two or more heartbeats, the trained model 21 is configured, for example, to output the coordinates of the E-wave and the A-wave in each of the Doppler waveforms as an E-wave/A-wave detection result. However, possible embodiments are not limited to this example. Alternatively, out of the Doppler waveforms corresponding to the two or more heartbeats, the trained model 21 may be configured to output the coordinates of the E-wave and the A-wave in a Doppler waveform corresponding to at least one heartbeat, as a result of the E-wave/A-wave detecting process.

Further, the trained model is not bound by image quality of the Doppler waveform image data input thereto. For example, the Doppler waveform image data input to the trained model may be any of the following: image data containing much noise; image data containing aliasing of the Doppler waveform; and image data having low brightness levels.

The trained model is generated by implementing a machine learning process on a multi-layered network, for example, while using training data (learning data) including sets made up of: a plurality of pieces of Doppler waveform image data each including a Doppler waveform corresponding to at least one heartbeat; and supervisor data (correct answer data) represented by the coordinates of the E-wave and the A-wave in the Doppler waveform with respect to a different one of the plurality of pieces of Doppler waveform image data. The multi-layered network denotes, for example, a machine learning model such as a Deep Neural network (hereinafter, "DNN"), a Convolution Neural Network (hereinafter, "CNN"), or the like. The training on the multi-layered network corresponds to adjusting a plurality of parameters used in the multi-layered network. In this situation, models on which the machine learning process can be implemented are not limited to multi-layered networks. It is possible to use an arbitrary model, as long as it is possible to maintain the relationship between the inputs and the outputs to and from the trained model.

It is possible to generate the supervisor data included in the training data, i.e., the coordinates of the E-wave and the A-wave in the Doppler waveform included in each of the pieces of Doppler waveform image data, for example, by using an existing algorithm or on the basis of a human process performed by a medical doctor or a medical technologist. A process (hereinafter, "model generating process") related to generating the trained model will be explained later.

For example, the image memory 83 includes a recording medium (e.g., a semiconductor memory) readable by a processor. For example, the image memory 83 is realized by using a cache memory. The image memory 83 is configured to save therein the data of various types of images acquired during a certain period preceding the freeze operation input via the input device 3. More specifically, to realize the scroll display, the image memory 83 is configured to store therein the Doppler waveform image data taken during the prescribed time period preceding the moment at which the freeze button is pressed, so as not to be overwritten by other data. Further, the internal storage circuit 81 and the image memory 83 may be integrated together as a single storage device.

The communication interface 85 is connected to an external device via a network. The communication interface 85 is configured to perform data communication with the external device via the network. The external device may be, for example, a medical image management system (e.g., a Picture Archiving and Communication System [PACS]), which is a system configured to manage data of various types of medical images, or an electronic medical record system configured to manage electronic medical records to which medical images are attached. Although any standard may be used as the standard for the communication with the external device, possible examples of the standard include Digital Imaging and COmmunications in Medicine (DICOM).

For example, the processing circuit 87 is a processor configured to function as a core of the ultrasound diagnosis apparatus 100. As hardware resources thereof, the processing circuit 87 includes a processor such as a Central Processing Unit (CPU) or a Micro Processing unit (MPU) and a memory such as a Read-Only Memory (ROM) and/or a Random Access Memory (RAM). Further, the processing circuit 87 may be realized by using an Application Specific Integrated Circuit (ASIC), a Field Programmable Gate Array (FPGA), or any of other devices such as a Complex Programmable Logic Device (CPLD) or a Simple Programmable Logic Device (SPLD).

For example, the processing circuit 87 includes various types of functions such as the system controlling function 871, an obtaining function 873, the detecting function 875, and a display controlling function 877. By loading various types of programs stored in the internal storage circuit 81 into a memory of its own and executing the loaded programs, the processing circuit 87 is configured to execute the system controlling function 871, the obtaining function 873, the detecting function 875, and the display controlling function 877 corresponding to the programs. Alternatively, instead of saving the programs in the internal storage circuit 81, it is also acceptable to directly incorporate the programs in the circuit of the processor. In that situation, the processor is configured to realize the functions by reading and executing the programs incorporated in the circuit thereof.

The processing circuit 87 configured to execute the system controlling function 871, the obtaining function 873, the detecting function 875, and the display controlling function 877 correspond to a system controlling unit, an obtaining unit, a detecting unit, and a display controlling unit. In this situation, the system controlling function 871, the obtaining function 873, the detecting function 875, and the display controlling function 877 do not each necessarily have to be realized by using a single processing circuit. It is also acceptable to structure a processing circuit by combining together a plurality of independent processors, so that the system controlling function 871, the obtaining function 873, the detecting function 875, and the display controlling function 877 are realized as a result of the processors executing the programs.

By employing the system controlling function 871, the processing circuit 87 is configured to control basic operations of the ultrasound diagnosis apparatus 100 such as inputting and outputting information. When the system controlling function 871 is executed, the processing circuit 87 receives an input designating any of various types of scan modes, via the input device 3, for example. In accordance with the received scan mode, the processing circuit 87 performs the designated one of various types of ultrasound scans and generates one or more of various types of ultrasound images. For example, when the scan mode is the pulse Doppler mode, the processing circuit 87 generates pieces of Doppler waveform image data in a time series, by controlling the ultrasound transmission circuit 71, the ultrasound reception circuit 73, the Doppler processing circuit 77, and the image generating circuit 79.

By employing the obtaining function 873, the processing circuit 87 is configured to obtain Doppler waveform image data acquired by scanning, in the pulse Doppler mode, the left ventricular blood inflow in the vicinity of the mitral valve of the patient P. More specifically, when a freeze operation is input via the input device 3 in the real-time display mode, the processing circuit 87 obtains the Doppler waveform image data displayed on the display device 5. As being triggered by the input of the freeze operation, the processing circuit 87 obtains the trained model from the internal storage circuit 81. Alternatively, instead of being triggered by the input of the freeze operation, the processing circuit 87 may obtain the Doppler waveform image data displayed on the display device 5, as being triggered by an input of an instruction to perform the E-wave/A-wave detecting process (hereinafter, "E-wave/A-wave detection instruction"). Further, when the trained model is stored in the memory of the processing circuit 87 itself, the processing circuit 87 obtains the trained model from the memory of its own, as being triggered by the input of the freeze operation or the like.

By employing the detecting function 875, the processing circuit 87 is configured to detect, with the use of the trained model, the coordinates of the E-wave and the A-wave in the Doppler waveform included in the Doppler waveform image data, by inputting the Doppler waveform image data to the trained model. More specifically, the processing circuit 87 is configured to detect the coordinates of the E-wave and the A-wave in the Doppler waveform included in the Doppler waveform image data, by inputting the Doppler waveform image data of the patient P to the trained model as first Doppler waveform data. On the basis of the detected coordinates of the E-wave and the A-wave, the processing circuit 87 is configured to calculate, with respect to each heartbeat: a flow velocity value MVE corresponding to the E-wave; a flow velocity value MVA corresponding to the A-wave; deceleration time DcT of the E-wave, a ratio MVE/MVA (E/A) between the E-wave flow velocity value MVE and the A-wave flow velocity value MVA; and the like. In this situation, the flow velocity value MVE, the flow velocity value MVA, and the like based on the detected coordinates of the E-wave and the A-wave may be calculated from a graph in the Doppler waveform image data input to the trained model or may be calculated from the Doppler data generated by the Doppler processing circuit 77.

Further, together with the coordinates of the E-wave and A-wave for each heartbeat, the trained model may output, with respect to each heartbeat, the flow velocity value MVE corresponding to the E-wave; the flow velocity value MVA corresponding to the A-wave; the deceleration time DcT of the E-wave; and the flow velocity ratio MVE/MVA (E/A). Further, the processing circuit 87 may store, into the internal storage circuit 81, the coordinates of the E-wave and the A-wave for each heartbeat that were output from the trained model so as to be kept in association with the corresponding Doppler waveform included in the Doppler image data input to the trained model.

By employing the display controlling function 877 and on the basis of the detected coordinates of the E-wave and the A-wave for each heartbeat, the processing circuit 87 is configured to map the positions of the E-wave and the A-wave for each heartbeat over the corresponding Doppler waveform. The processing circuit 87 is configured to cause the display device 5 to display Doppler waveform image data obtained by superimposing the positions (the coordinates) of the E-wave and the A-wave for each heartbeat over the corresponding Doppler waveform. More specifically, on the basis of the detected coordinates of the E-wave and the A-wave for each heartbeat, the processing circuit 87 is configured to cause the display device 5 to display the Doppler waveform image data in which the positions of the corresponding E-wave and A-wave are indicated by guide elements in each Doppler waveform.

The E-Wave/A-Wave Detecting Process

Figure 3:
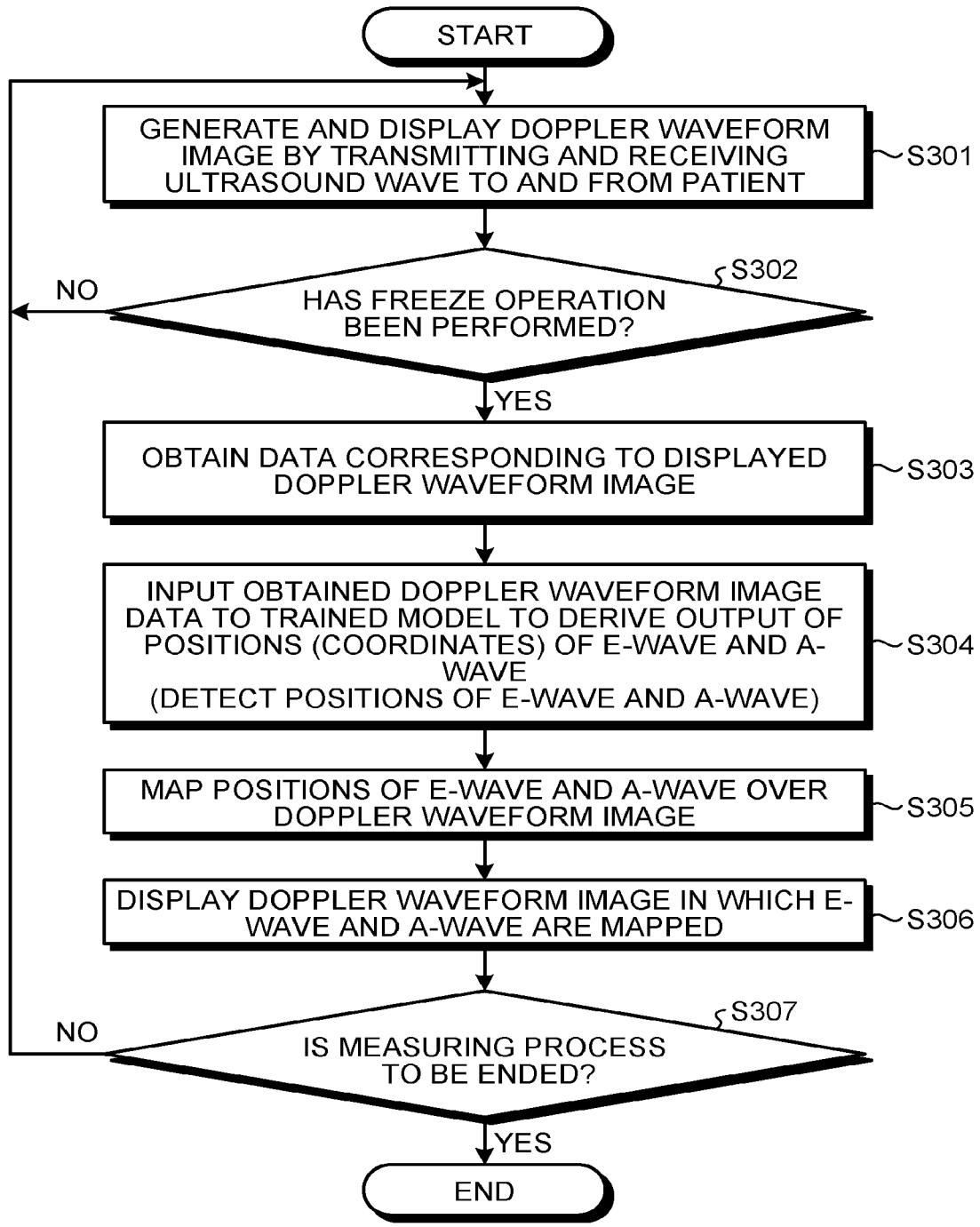
FIG. 3 is a flowchart illustrating an example of a flow in an E-wave/A-wave detecting process.

Next, the E-wave/A-wave detecting process performed by the ultrasound diagnosis apparatus 100 will be explained. FIG. 3 is a flowchart illustrating an example of a flow in the E-wave/A-wave detecting process. To explain a specific example, it is assumed that the trained model is configured to receive an input of Doppler waveform image data acquired by scanning, in the pulse Doppler mode, the left ventricular blood inflow in the vicinity of the mitral valve of the patient P and configured to output the coordinates of the E-wave and the A-wave in the Doppler waveform corresponding to each heartbeat included in the Doppler waveform image data. In addition, it is assumed that the Doppler waveform image data is input to the trained model as being triggered by a freeze operation performed in the real-time display mode.

Step S301:

As a result of transmitting and receiving an ultrasound wave to and from the patient P, the Doppler processing circuit 77 generates Doppler-mode raw data and stores the generated Doppler-mode raw data into the raw data memory. On the basis of the Doppler-mode raw data read from the raw data memory, the image generating circuit 79 generates Doppler waveform image data. The display device 5 displays a Doppler waveform image. In this situation, while the scroll display mode is implemented, the display device 5 displays, at the present step, a Doppler waveform corresponding to at least one corresponding heartbeat, in accordance with the scroll operation.

Step S302:

When a freeze operation is performed via the input device 3 (step S302: Yes), the process at step S303 is performed. On the contrary, when no freeze operation is performed via the input device 3 (step S302: No), the process at step S301 is performed. While the scroll display mode is implemented, when an instruction to perform the E-wave/A-wave detecting process is input via the input device 3 (e.g., when a button for the E-wave/A-wave detecting process is pressed), the process at step S303 is performed. On the contrary, while the scroll display mode is implemented, when no instruction to perform the E-wave/A-wave detecting process is input via the input device 3 at the present step, the abovementioned scroll display is carried out at step S301.

Step S303:

By employing the obtaining function 873, the processing circuit 87 obtains, from the internal storage circuit 81 or the image memory 83, the data corresponding to the Doppler waveform image displayed on the display device 5. The processing circuit 87 reads the trained model from the internal storage circuit 81. In this situation, the Doppler waveform image displayed on the display device 5 may contain much noise, may have the occurrence of aliasing of a Doppler waveform, may have low brightness levels, or the like. Further, it is sufficient when the Doppler waveform image displayed on the display device 5 includes a Doppler waveform corresponding to at least one heartbeat.

Step S304:

By employing the detecting function 875, the processing circuit 87 inputs the obtained Doppler waveform image data to the trained model. Accordingly, by using the trained model, the processing circuit 87 outputs the coordinates of the E-wave and the A-wave with respect to the Doppler waveform corresponding to each of the heartbeats included in the Doppler waveform image data that was input.

Step S305:

By employing the display controlling function 877 and on the basis of the coordinates of the E-wave and the A-wave with respect to the Doppler waveform corresponding to each of the heartbeats, the processing circuit 87 maps the positions of the E-wave and the A-wave for each heartbeat over the corresponding Doppler waveform. As a result, Doppler waveform image data is generated in which the positions (the coordinates) of the E-wave and the A-wave for each heartbeat are superimposed over the corresponding Doppler waveform.

Step S306:

On the basis of the detected coordinates of the E-wave and the A-wave for each heartbeat, the processing circuit 87 causes the display device 5 to display the Doppler waveform image data in which the positions of the corresponding E-wave and A-wave are indicated by the guide elements in each of the Doppler waveforms. The display device 5 displays the Doppler waveform image in which the positions of the E-wave and the A-wave are indicated by the guide elements.

Figure 4:
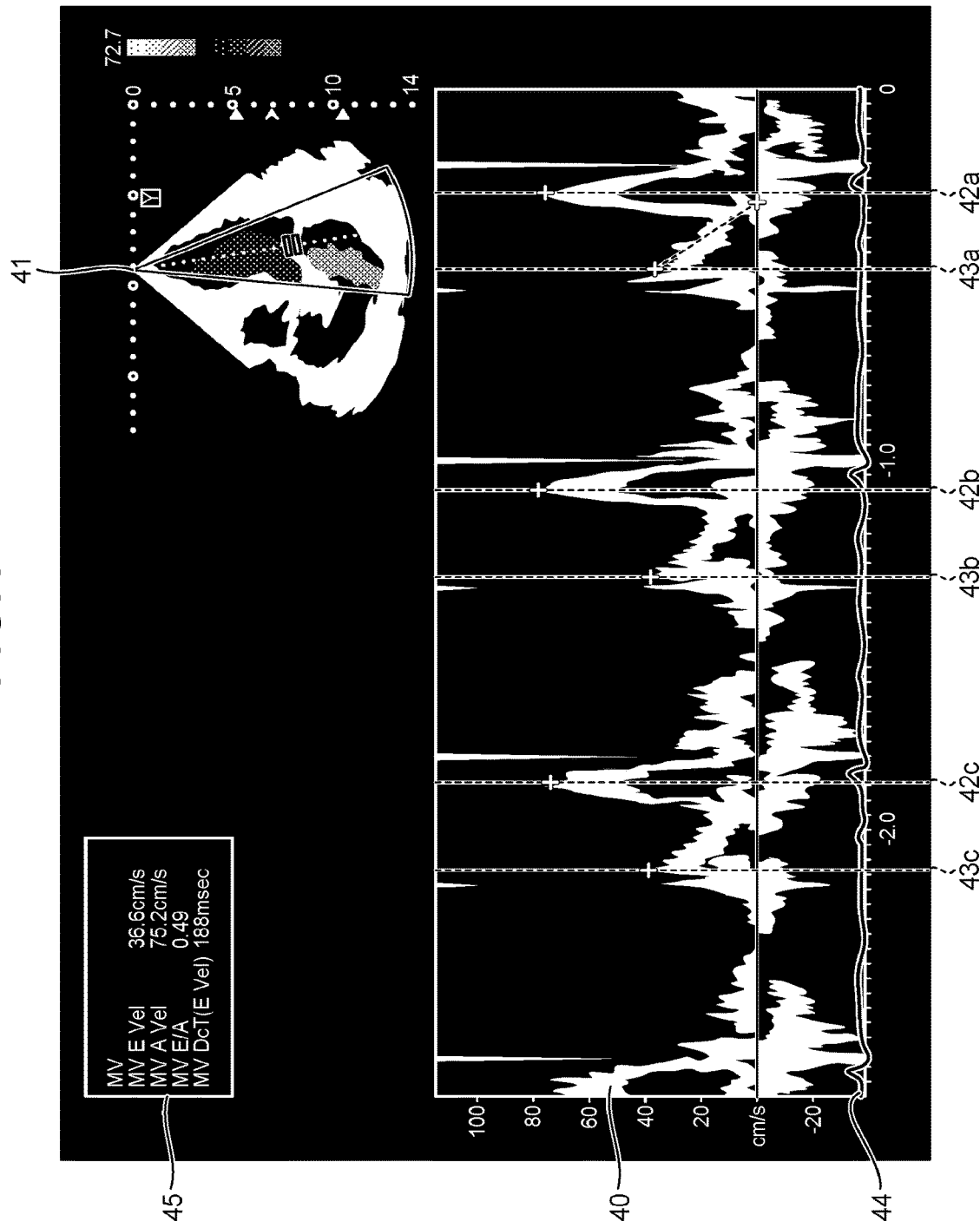
FIG. 4 is a drawing illustrating an example of a Doppler waveform image displayed on a display device as a result of the E-wave/A-wave detecting process according to the embodiment.

FIG. 4 is a drawing illustrating an example of the Doppler waveform image displayed on the display device 5 as a result of the E-wave/A-wave detecting process according to an embodiment. As illustrated in FIG. 4, the display device 5 displays, a Doppler waveform image 40 corresponding to three heartbeats, a color Doppler image 41, E-wave guide elements 42a, 42b, and 42c, A-wave guide elements 43a, 43b, and 43c, an Electrocardiogram (ECG) waveform 44, and indices 45. In other words, in the example in FIG. 4, the positions of the E-wave and the A-wave in the Doppler waveform for each of the heartbeats within the Doppler waveform image 40 are indicated by the E-wave guide elements 42a, 42b, and 42c and the A-wave guide elements 43a, 43b, and 43c that are displayed as being superimposed over the Doppler waveform image 40. In the present example, of the E-wave guide elements and the A-wave guide elements, the broken lines indicate positions on the time axis, whereas the "+" symbols indicate positions in the Doppler waveform. Further, the indices 45 display, with respect to the Doppler waveform corresponding to a selected heartbeat, an E-wave flow velocity value MVE, an A-wave flow velocity value MVA, a ratio MVE/MVA (E/A) between the E-wave flow velocity value MVE and the A-wave flow velocity value MVA, and deceleration time DcT of the E-wave, and/or the like.

Step S307:

When an instruction to end the E-wave/A-wave detecting process is input via the input device 3 (step S307: Yes), the E-wave/A-wave detecting process ends. On the contrary, when no instruction to end the E-wave/A-wave detecting process is input via the input device 3 (step S307: No), the processes at step S301 and thereafter are repeatedly performed.

A Model Generating Process

Figure 5:
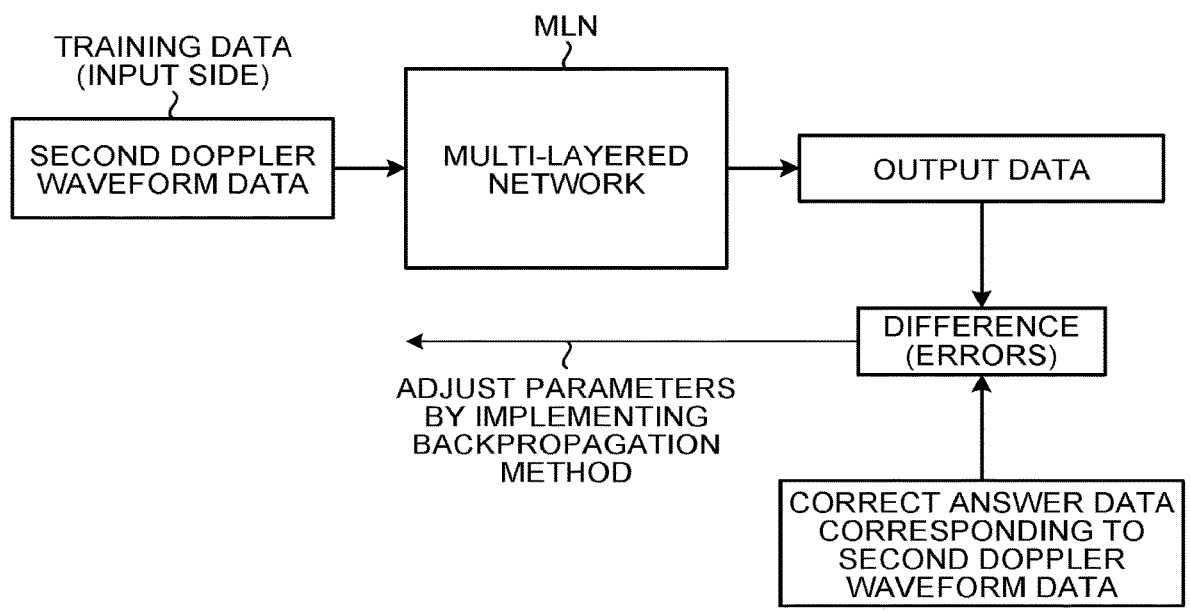
FIG. 5 is a diagram illustrating an example of inputs and outputs of data to cause a multi-layered network to perform a learning process during a model generating process according to the embodiment.

Next, a model generating process for generating the trained model will be explained, with reference to FIG. 5. FIG. 5 is a diagram illustrating an example of inputs and outputs of data to cause a multi-layered network MLN to perform a learning process during the model generating process according to the embodiment. The trained model generating process is performed, for example, by a training device different from the ultrasound diagnosis apparatus 100. The training device is realized by using a stand-alone (independent) computer, a server provided on a network, or the like. Further, it is assumed that the aforementioned learning-purpose data is stored in a memory or a storage device installed in the training device or a training data storage device.

In the following sections, to explain a specific example, a plurality of pieces of second Doppler waveform data that are input to the multi-layered network MLN as training data include, for example, one or both of: waveform data containing much noise and aliasing waveform data. In the present example, the waveform data containing much noise denotes Doppler waveform data containing noise equal to or higher than a certain reference level, in addition to a Doppler waveform corresponding to at least one heartbeat. The aliasing waveform data denotes Doppler waveform data including a Doppler waveform corresponding to at least one heartbeat and having the occurrence of aliasing. In the present embodiment, to explain a specific example, it is assumed that the plurality of pieces of second Doppler waveform data that are input to the multi-layered network MLN as the training data include: waveform data containing much noise, aliasing waveform data, and normal waveform data (Doppler waveform data including a Doppler waveform which has noise equal to or lower than a reference value, has no occurrence of aliasing, and corresponds to at least one heartbeat).

Further, the second Doppler waveform data used as the training data includes a Doppler waveform corresponding to a plurality of types of quantities of heartbeats. In other words, the Doppler waveform included in the second Doppler waveform data used as the training data may correspond to an arbitrary number of heartbeats. Typically, it is possible to use second Doppler waveform data including a Doppler waveform corresponding to three to five heartbeats.

Figure 6:
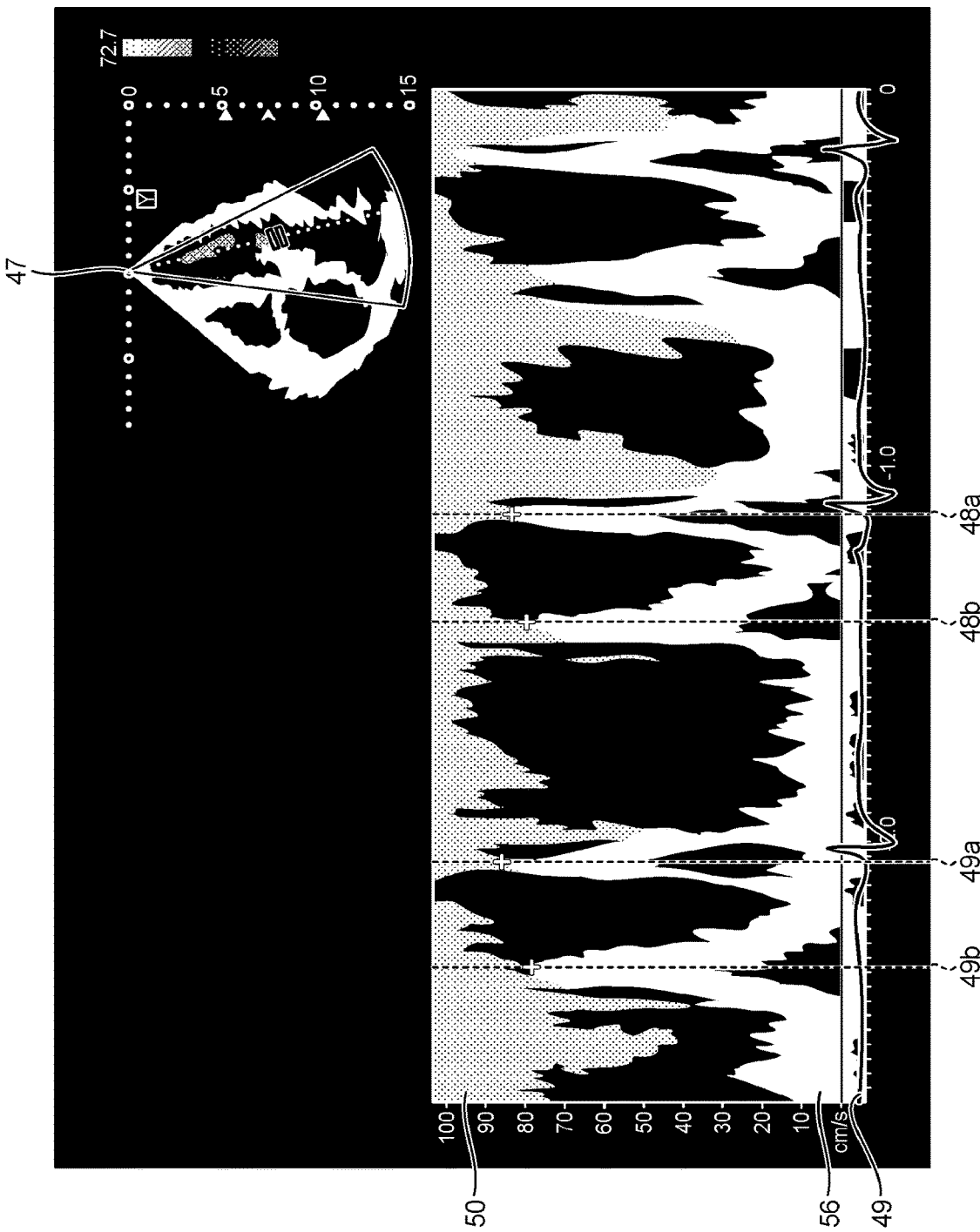
FIG. 6 is a drawing illustrating an example of a Doppler mode display screen that includes waveform data containing much noise and is used for generating the trained model.

FIG. 6 is a drawing illustrating an example of a Doppler mode display screen that includes the waveform data containing much noise and is used for generating the trained model. The Doppler mode display screen illustrated in FIG. 6 displays a Doppler waveform image corresponding to two heartbeats 56, a color Doppler image 47, E-wave guide elements 48a and 49a, A-wave guide elements 48b and 49b, and an ECG waveform 49. Further, the Doppler waveform image corresponding to two heartbeats 56 illustrated in FIG. 6 and serving as the waveform data containing much noise includes, for example, a large amount of noise like haze (which is illustrated as hatched region 50 in FIG. 6). The correct answer data corresponding to the waveform data containing much noise illustrated in FIG. 6 is indicated by the coordinates of the "+" symbols of the E-wave guide elements 48a and 49a and the A-wave guide elements 48b and 49b in FIG. 6.

FIG. 7 is a drawing illustrating an example of a Doppler mode display screen that includes the aliasing waveform data and is used for generating the trained model. The Doppler mode display screen illustrated in FIG. 7 displays a Doppler waveform image corresponding to three heartbeats 51, a color Doppler image 53, E-wave guide elements 56a, 57a, and 58a, A-wave guide elements 56b, 57b, and 58b, and an ECG waveform 55. Further, the Doppler waveform image corresponding to three heartbeats 51 illustrated in FIG. 7 and serving as the aliasing waveform includes an aliasing waveform 52 in each of the heartbeats. The correct answer data corresponding to the aliasing waveform data illustrated in FIG. 7 is indicated by the coordinates of the "+" symbols of the E-wave guide elements 56a, 57a, and 58a and the A-wave guide elements 56b, 57b, and 58b in FIG. 7.

FIG. 8 is a drawing illustrating an example of a Doppler mode display screen that includes the normal waveform data and is used for generating the trained model. The Doppler mode display screen illustrated in FIG. 8 displays a Doppler waveform image corresponding to four heartbeats 61 serving as the normal waveform data, a color Doppler image 62, E-wave guide elements 66a, 67a, 68a, and 69a, A-wave guide elements 66b, 67b, 68b, and 69b, and an ECG waveform 63. Also, in the example of the Doppler mode display screen in FIG. 8, indices 64 are further displayed to indicate the E-wave flow velocity value MVE and the like with respect to each of the heartbeats. The correct answer data corresponding to the normal waveform data illustrated in FIG. 8 is indicated by the coordinates of the "+" symbols of the E-wave guide elements 66a, 67a, 68a, 69a and the A-wave guide elements 66b, 67b, 68b, and 69b in FIG. 8.

As illustrated in FIG. 5, the pieces of second Doppler waveform data illustrated in FIGS. 6 to 8 are input to the multi-layered network MLN. The training device is configured to calculate the difference between output data from the multi-layered network MLN and the correction data corresponding to the second Doppler waveform data input to the multi-layered network MLN. The training device is configured to adjust a plurality of parameters in the multi-layered network MLN by implementing a backpropagation method, for example, so that the calculated difference (errors) is equal to or smaller than a prescribed value. The training device is configured to input second Doppler waveform data different from the second Doppler waveform data used for the adjustment, to the multi-layered network MLN of which the plurality of parameters have been adjusted. After that, the training device is configured to further adjust the plurality of parameters in the multi-layered network MLN in the same manner. For the training process performed on the multi-layered network MLN, because it is possible to use, as appropriate, an existing method such as that described in Non-Patent Literature 1, for example, explanations thereof will be omitted.

As explained above, the ultrasound diagnosis apparatus 100 according to the embodiment includes the obtaining function 873 serving as an obtaining unit and the detecting function 875 serving as a detecting unit. The obtaining function 873 is configured to obtain the first Doppler waveform data related to the left ventricular blood inflow. The detecting function 875 is configured to detect the positions of the E-wave and the A-wave in the first Doppler waveform data, by using the first Doppler waveform data and the trained model trained with the training data that includes at least the positions of the E-wave and the A-wave in each of the plurality of pieces of second Doppler waveform data related to the left ventricular blood inflow and the plurality of pieces of second Doppler waveform data.

More specifically, first ultrasound image data and second ultrasound image data correspond to the Doppler waveform image data. By using the ultrasound diagnosis apparatus 100 according to the embodiment, it is possible, by using the trained model, to detect the positions of the E-wave and the A-wave with respect to the Doppler waveform corresponding to each of the heartbeats included in the first ultrasound image data and to further cause the detected positions of the E-wave and the A-wave to be displayed while being superimposed over the Doppler waveform image corresponding to the first ultrasound image data.

Further, the trained model is, for example, the multi-layered network MLN trained by using the waveform data containing much noise, the aliasing waveform data, the Doppler waveform data having low brightness levels, and the like. Accordingly, even when the first ultrasound image data input to the trained model contains noise and aliasing or is image data in which the Doppler waveform has low visibility, it is possible to accurately identify the positions of the E-wave and the A-wave.

Further, the trained model is, for example, the multi-layered network MLN trained by using the data including the Doppler waveform corresponding to the plurality of types of quantities of heartbeats, or the like. Accordingly, regardless of the number of Doppler waveforms included in the first ultrasound image data input to the trained model, it is possible to accurately identify the positions of the E-wave and the A-wave.

Consequently, by using the ultrasound diagnosis apparatus 100 according to the embodiment, it is possible to automatically detect the accurate E-wave and A-wave with respect to the Doppler waveform corresponding to each of the heartbeats and to cause the detected positions to be displayed while being superimposed over the Doppler waveform image, even in the situations where the existing algorithms or human processes would find it difficult to perform the E-wave/A-wave detecting process, e.g., when the Doppler waveform image contains noise, aliasing, and/or the like. Consequently, by using the present apparatus, it is possible to improve throughput in the ultrasound image diagnosing processes on cardiac insufficiency.

First Modification Example

The above embodiment was explained by using the example of the trained model configured to receive the input of the Doppler waveform image data and to output the coordinates of the E-wave and the A-wave in the Doppler waveform within the Doppler waveform image data being input. Alternatively, it is also possible to use a trained model configured to receive an input of Doppler waveform image data that further includes, in addition to a Doppler waveform corresponding to one or more heartbeats, an ECG waveform obtained in synchronization with the Doppler waveform corresponding to the one or more heartbeats and configured to output the coordinates of an E-wave and an A-wave in each of the Doppler waveforms within the Doppler waveform image data.

To generate the trained model described above, the following training data may be used: The input data is the Doppler waveform image data that further includes the ECG waveform obtained in synchronization with the Doppler waveform corresponding to the one or more heartbeats, in addition to the Doppler waveform corresponding to the one or more heartbeats. Further, with respect to each of the pieces of input data, the coordinates of the E-wave and the A-wave in the Doppler waveform are used as supervisor data. By using training data including a plurality of sets each made up of the input data and the supervisor data described above, the trained model is generated by implementing a machine learning process on a multi-layered network, for example.

Further, when necessary, it is also acceptable to use a trained model configured to receive an input of image data of an exhalation waveform obtained in synchronization with the Doppler waveform included in the Doppler waveform image data, either together with the image data of the ECG waveform or in place of the image data of the ECG waveform and configured to output the coordinates of the E-wave and the A-wave in the Doppler waveform within the Doppler waveform image data. In this situation also, the image data of the exhalation waveform may be included in the Doppler waveform image data or may be separate data from the Doppler waveform image data.

For example, to generate the trained model described above configured to receive the input of the image data of the exhalation waveform and the ECG waveform obtained in synchronization with the Doppler waveform included in the Doppler waveform image data, the following training data may be used: The input data is the Doppler waveform image data that further includes, in addition to the Doppler waveform corresponding to one or more heartbeats, the ECG waveform and the exhalation waveform obtained in synchronization with the Doppler waveform corresponding to the one or more heartbeats. Further, with respect to each of the pieces of input data, the coordinates of the E-wave and the A-wave in the Doppler waveform are used as supervisor data. By using training data including a plurality of sets each made up of the input data and the supervisor data described above, the trained model is generated by implementing a machine learning process on a multi-layered network, for example.

Second Modification Example

In the above embodiment, the example was explained in which the display device 5 is caused to display the Doppler waveform image data obtained by superimposing, over the corresponding Doppler waveform, the positions (the coordinates) of the E-wave and the A-wave in each of the heartbeats detected by the trained model. Alternatively, it is also acceptable to configure the trained model so as to output the Doppler waveform image data obtained by superimposing, over the corresponding Doppler waveform, the detected positions of the E-wave and the A-wave in each of the heartbeats. In this situation, the trained model is caused by the detecting function 875 to receive an input of the Doppler waveform image data including a Doppler waveform corresponding to at least one heartbeat and to output the Doppler waveform image data obtained by superimposing the positions of the E-wave and the A-wave in each of the heartbeats over the corresponding Doppler waveform.

Third Modification Example

In the above embodiment, the example was explained in which the Doppler waveform image data generated by the image generating circuit 79 is input to the trained model so as to perform the E-wave/A-wave detecting process. Alternatively, it is also possible to perform the E-wave/A-wave detecting process by inputting, to a trained model, the Doppler waveform data (i.e., the Doppler raw data stored in the raw data memory) generated by the Doppler processing circuit 77, as the first Doppler waveform data. In that situation, the model configured to perform the E-wave/A-wave detecting process is generated by using training data that uses the Doppler raw data as the second Doppler waveform data and uses the coordinates of the E-wave and the A-wave in the second Doppler waveform data as supervisor data.

Fourth Modification Example

In the above embodiment, the example was explained in which the apparatus is the ultrasound diagnosis apparatus 100. Alternatively, the apparatus according to the present embodiment may be realized by using, for example, a medical image processing apparatus, a medical image processing server apparatus, a workstation, or cloud computing. The medical image processing apparatus, the medical image processing server apparatus, the workstation, or the cloud computing has, for example, the configuration indicated within the dotted-line frame 9 in FIG. 1. When the apparatus is realized as a medical image processing apparatus, a medical image processing server apparatus, a workstation, or cloud computing, the input device 3 and the display device 5 may be, for example, connected to a network as client devices. In that situation, for example, the internal storage circuit 81, the image memory 83, the communication interface 85, and the processing circuit 87 may be installed in a server provided on the network.

When the technical concepts of any of the present embodiments and the present application examples are realized by using a program such as a medical image processing program, the program is configured to cause a computer to realize: obtaining first Doppler waveform data related to a left ventricular blood inflow; and detecting the positions of an E-wave and an A-wave in the first Doppler waveform data by using the first Doppler waveform data and the trained model trained with the training data that includes at least the positions of the E-wave and the A-wave in each of the plurality of pieces of second Doppler waveform data related to the left ventricular blood inflow and the plurality of pieces of second Doppler waveform data. For example, it is also possible to realize the E-wave/A-wave detecting process by installing the program onto a PACS server and an integrated server in a hospital information system as well as a computer of the ultrasound diagnosis apparatus 100 and the like and further loading the respective programs into a memory. In that situation, the programs each capable of causing the computer to execute the method may be distributed as being stored in a storage medium such as a magnetic disk (e.g., a hard disk), an optical disc (e.g., a Compact Disc Read-Only Memory [CD-ROM], a Digital Versatile Disc [DVD]), or a semiconductor memory. Because the processing procedures and the advantageous effects of the programs are the same as those described in the embodiments, the explanations thereof will be omitted.

According to at least one aspect of the embodiments and the modification examples described above, it is possible to accurately identify the positions of the E-wave and the A-wave, even when the Doppler waveform image contains much noise, aliasing, and/or the like.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An apparatus, comprising:
  processing circuitry configured to:
    obtain first Doppler waveform data related to a left ventricular blood inflow; and
    detect positions of an Early Wave (E-wave) and an Atrium Wave (A-wave) in the first Doppler waveform data, by using the first Doppler waveform data and a trained model trained with training data that includes at least positions of an E-wave and an A-wave in each of a plurality of pieces of second Doppler waveform data related to left ventricular blood inflows and the plurality of pieces of second Doppler waveform data,
  wherein the plurality of pieces of second Doppler waveform data include at least Doppler waveform data containing noise equal to or higher than a reference value.

2. The apparatus according to claim 1, wherein
  the processing circuitry is further configured to obtain an electrocardiogram (ECG) waveform synchronized with a Doppler waveform included in the first Doppler waveform data, and the processing circuitry is further configured to detect the positions of the E-wave and the A-wave in the first Doppler waveform data, by using the first Doppler waveform data and the trained model trained with the training data that further includes an ECG waveform.

3. The apparatus according to claim 1, wherein
the processing circuitry is further configured to obtain an exhalation waveform synchronized with a Doppler waveform included in the first Doppler waveform data, and
the processing circuitry is further configured to detect the positions of the E-wave and the A-wave in the first Doppler waveform data, by using the first Doppler waveform data and the trained model trained with the training data that further includes an exhalation waveform.

4. The apparatus according to claim 1, wherein the plurality of pieces of second Doppler waveform data include a Doppler waveform corresponding to different numbers of heartbeats.

5. The apparatus according to claim 1, wherein the plurality of pieces of second Doppler waveforms data include a Doppler waveform corresponding to a plurality of heartbeats.

6. The apparatus according to claim 1, wherein, when the first Doppler waveform data includes a Doppler waveform corresponding to a plurality of heartbeats, the processing circuitry is further configured to detect the positions of the E-wave and the A-wave with respect to a Doppler waveform corresponding to each of the heartbeats.

7. The apparatus according to claim 1, wherein, by using coordinates of the detected E-wave and A-wave and the first Doppler waveform data, the processing circuitry is further configured to cause a display circuit to display an image in which the positions of the E-wave and the A-wave are superimposed over the first Doppler waveform data.

8. An apparatus, comprising:
processing circuitry configured to
obtain first Doppler waveform data related to a left ventricular blood inflow; and
detect positions of an Early Wave (E-wave) and an Atrium Wave (A-wave) in the first Doppler waveform data, by using the first Doppler waveform data and a trained model trained with training data that includes at least positions of an E-wave and an A-wave in each of a plurality of pieces of second Doppler waveform data related to left ventricular blood inflows and the plurality of pieces of second Doppler waveform data,
wherein the plurality of pieces of second Doppler waveform data include at least Doppler waveform data containing aliasing of a Doppler waveform.

9. A data processing method, comprising:
obtaining first Doppler waveform data related to a left ventricular blood inflow; and
detecting positions of an Early Wave (E-wave) and an Atrium Wave (A-wave) in the first Doppler waveform data, by using the first Doppler waveform data and a trained model trained with training data that includes at least positions of an E-wave and an A-wave in each of a plurality of pieces of second Doppler waveform data related to left ventricular blood inflows and the plurality of pieces of second Doppler waveform data,
wherein the plurality of pieces of second Doppler waveform data include at least Doppler waveform data containing noise equal to or higher than a reference value.

10. The data processing method according to claim 9, further comprising:
obtaining an electrocardiogram (ECG) waveform synchronized with a Doppler waveform included in the first Doppler waveform data, and
detecting the positions of the E-wave and the A-wave in the first Doppler waveform data, by using the first Doppler waveform data and the trained model trained with the training data that further includes an ECG waveform.

11. The data processing method according to claim 9, further comprising:
obtaining an exhalation waveform synchronized with a Doppler waveform included in the first Doppler waveform data is obtained, and
detecting the positions of the E-wave and the A-wave in the first Doppler waveform data, by using the first Doppler waveform data and the trained model trained with the training data that further includes an exhalation waveform.

12. The data processing method according to claim 9, wherein the plurality of pieces of second Doppler waveform data include a Doppler waveform corresponding to different numbers of heartbeats.

13. The data processing method according to claim 9, wherein the plurality of pieces of second Doppler waveform data include a Doppler waveform corresponding to a plurality of heartbeats.

14. The data processing method according to claim 9, wherein, when the first Doppler waveform data includes a Doppler waveform corresponding to a plurality of heartbeats, the method further comprises detecting the positions of the E-wave and the A-wave with respect to a Doppler waveform corresponding to each of the heartbeats.

15. The data processing method according to claim 9, further comprising, by using coordinates of the detected E-wave and A-wave and the first Doppler waveform data, causing a display circuit to display an image in which the positions of the E-wave and the A-wave are superimposed over the first Doppler waveform data.

16. A data processing method, comprising:
obtaining first Doppler waveform data related to a left ventricular blood inflow; and
detecting positions of an Early Wave (E-wave) and an Atrium Wave (A-wave) in the first Doppler waveform data, by using the first Doppler waveform data and a trained model trained with training data that includes at least positions of an E-wave and an A-wave in each of a plurality of pieces of second Doppler waveform data related to left ventricular blood inflows and the plurality of pieces of second Doppler waveform data,
wherein the plurality of pieces of second Doppler waveform data include at least Doppler waveform data containing aliasing of a Doppler waveform.

* * * * *